US00PP33856P2

(12) United States Plant Patent
Li

(10) Patent No.: US PP33,856 P2
(45) Date of Patent: Jan. 11, 2022

(54) ***VERBENA* PLANT NAMED 'KLEVP20052'**

(50) Latin Name: ***Verbena* x *hybrida***
Varietal Denomination: KLEVP20052

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/332,662

(22) Filed: May 27, 2021

(51) Int. Cl.
*A01H 6/86* (2018.01)
*A01H 5/02* (2018.01)

(52) U.S. Cl.
USPC ..... Plt./308

(58) Field of Classification Search
USPC ..... Plt./308
See application file for complete search history.

*Primary Examiner* — Annette H Para
(74) *Attorney, Agent, or Firm* — Weatherly IP Solutions, LLC; Barbara Campbell

(57) ABSTRACT

A new *Verbena* plant particularly distinguished by red and light violet flowers with white at the base of the petals, and an upright, compact, and rounded habit, is disclosed.

1 Drawing Sheet

Genus and species: *Verbena* x *hybrida*.
Variety denomination: 'KLEVP20052'.

BACKGROUND OF THE NEW PLANT

The present invention comprises a new and distinct variety of *Verbena*, botanically known as *Verbena* x *hybrida*, and hereinafter referred to by the variety name 'KLEVP20052'. 'KLEVP20052' originated from a cross-pollination conducted in November 2015 in Cobbitty, New South Wales, Australia between the proprietary female *Verbena* variety '15.5169' (unpatented), and the proprietary male *Verbena* variety '15.5170' (unpatented).

The seeds from the cross were sown and plants were grown for evaluation, where an individual plant designated 'KLEVP20052' was selected from the group of plants in Cobbitty, New South Wales, Australia in October 2016.

In October 2016, 'KLEVP20052' was first vegetatively propagated by vegetative cuttings in Cobbitty, New South Wales, Australia. 'KLEVP20052' was found to reproduce true to type in successive generations of asexual propagation via vegetative stem cuttings.

SUMMARY

The following are the most outstanding and distinguishing characteristics of this new variety when grown under normal horticultural practices in Latina, Italy.

1. Red and light violet flowers with white at the base of the petals; and
2. Having an upright, compact, and rounded habit.

DESCRIPTION OF THE PHOTOGRAPH

This new *Verbena* plant is illustrated by the accompanying photograph which shows the plant's overall plant habit including form, foliage, and flowers. The photograph is of a plant approximately 12-weeks-old grown indoors in Stuttgart, Germany in April 2020. The colors shown are as true as can be reasonably obtained by conventional photographic procedures.

DESCRIPTION OF THE NEW VARIETY

The following detailed descriptions set forth the distinctive characteristics of 'KLEVP20052'. The data which define these characteristics were collected from asexual reproductions carried out in Latina, Italy. Data was collected on three-month-old plants grown in a greenhouse in 2019. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP20052'.

Parentage:
- *Female parent*.—'15.5169' (unpatented).
- *Male parent*.—'15.5170' (unpatented).

Plant:
- *Growth and branching habit*.—Upright with a compact and round shape.
- *Height* (*from top of soil*).—23.0 cm.
- *Width* (*horizontal plant diameter*).—34.0 cm.
- *Time to produce a finished flowering plant*.—Approximately 8 weeks.
- *Time to initiate and develop roots*.—2 weeks.
- *Root description*.—RHS 155B (White), fine fibrous roots.

Stems:
- *Number of branches per plant*.—More than 25.
- *Growth habit*.—Upright.
- *Length*.—20.0 cm.
- *Diameter*.—0.23 cm.
- *Internode length*.—2.0 cm.
- *Color*.—RHS 139D (Green).
- *Anthocyanin*.—Absent.

*Texture*.—Pubescent.
*Appearance in cross-section*.—Round.

Leaves:
*Arrangement*.—Opposite.
*Immature and mature leaf color*.—Upper surface: RHS 141A (Green). Lower surface: RHS 141C (Green).
*Length*.—4.1 cm.
*Width*.—2.1 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D (Green).
*Petioles*.—Length: 0.3 cm. Diameter: 0.1 cm. Color: RHS 141D (Green). Texture: Leathery.

Flower buds:
*Shape*.—Tall, cylindrical.
*Length*.—1.5 cm.
*Diameter*.—0.3 cm.
*Color* (*at tight bud*).—RHS 68C (Red-Purple).

Inflorescence:
*Blooming habit* (*flowering season*).—Continuously.
*Lastingness of individual blooms on the plant*.—About 1 week.
*Fragrance*.—Absent.
*Inflorescence type*.—Umbel.
*Length of inflorescence*.—4.7 cm.
*Diameter of inflorescence*.—5.0 cm.
*Number of florets per inflorescence*.—17.
*Peduncle*.—Color: RHS 141A (Green). Length: 2.6 cm. Diameter: 0.2 cm.

Florets:
*Length*.—1.8 cm.
*Diameter*.—1.7 cm.
*Texture*.—Smooth.
*Form*.—Single.
*Corolla tube length*.—1.8 cm.
*Corolla tube color*.—RHS 157B (Green-White).
*Petals*.—Length of lobe: 1.9 cm. Diameter of lobe: 0.9 cm. Lobe shape: Obtuse. Apex: Emarginate. Base: Fused. Margin: Entire. Texture (both upper and lower surfaces): Glossy, satiny. Color: Immature: Upper surface: Upper two petals are RHS 42B (Red) and the lower three petals, distally, are close to RHS N66C (Red-Purple) and proximally, close to RHS 155B (White). Lower surface: Upper two petals are RHS 51A (Red) and the lower three petals, distally, are close to RHS 69C (Red-Purple) and proximally, are close to RHS 155A (White). Mature: Upper surface: Upper two petals are RHS 42C (Red) and the lower three petals, distally, are close to RHS N66D (Red-Purple) and proximally, close to RHS 155D (White). Lower surface: Upper two petals are RHS 51B (Red) and the lower three petals are, distally, close to RHS 69C (Red-Purple) and proximally, close to RHS 155B (White).
*Pedicels*.—Not visible.

Sepals:
*Shape*.—Lanceolate.
*Apex*.—Acute.
*Base*.—Fused.
*Margin*.—Entire.
*Length*.—1.3 cm.
*Diameter*.—0.2 cm.
*Color*.—RHS 141C (Green).
*Texture* (*both upper and lower surfaces*).—Hairy, dull.

Reproductive organs:
*Stamens*.—Present. Quantity: 4. Appearance: Didynamous. Color: RHS 139D (Green). Filament length: 0.3 cm. Filament diameter: 0.1 cm. Anther: Shape: Elliptic. Color: RHS 141D (Green). Length: 0.15 cm. Diameter: 0.1 cm. Pollen amount: Moderate. Pollen color: RHS 1B (Green-Yellow).
*Pistils*.—Quantity: 1. Length: 1.7 cm. Diameter: 0.1 cm. Stigma: Color: RHS 141D (Green). Appearance: Ovate. Length: 0.1 cm. Diameter: 0.1 cm. Style: Color: RHS 141D (Green). Length: 1.5 cm. Diameter: 0.1 cm. Appearance: Long.

Fruit and seed set: None observed.

Disease and pest/insect resistance: Good tolerance to powdery mildew (*Podosphaera xanthii*).

COMPARISON WITH PARENTAL LINES AND KNOWN VARIETY

'KLEVP20052' is distinguished from its parents as described in Table 1.

TABLE 1

Comparison with Parental Lines

| Characteristic | 'KLEVP20052' | Female parent '15.5169' | Male parent '15.5170' |
|---|---|---|---|
| Flower color | Upper two petals are red, while the lower three petals are light violet | Upper two petals are burgundy, while the lower three petals are white | Upper two petals are deep pink, while the lower three petals are lavender |

'KLEVP20052' is most similar to the commercial *Verbena* POPS 'Salmon+Red Eye' (also known as 'KLEVP15616', U.S. Plant Pat. No. 28,320). Differences between the varieties are described in Table 2.

TABLE 2

Comparison with Similar Variety

| Characteristic | 'KLEVP20052' | 'Salmon + Red Eye' |
|---|---|---|
| Growth habit | Upright, compact, and rounded shape | Upright |
| Flower color | Bicolor | Solid with eyes |
| Branching ability | More branching than 'Salmon + Red Eye' | Less branching than 'KLEVP20052' |

I claim:

1. A new and distinct variety of *Verbena* plant designated 'KLEVP20052' as illustrated and described herein.

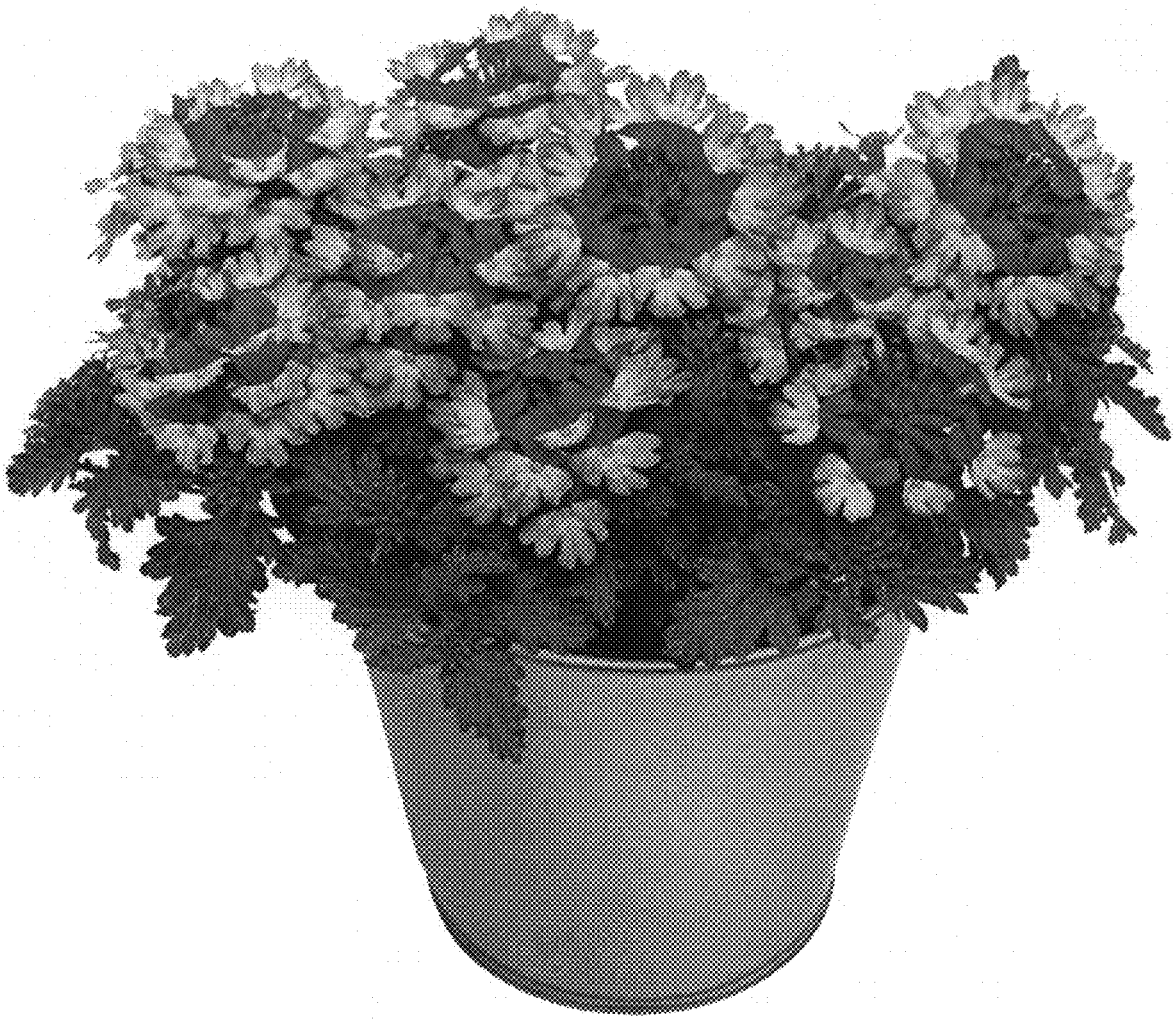

* * * * *